(12) United States Patent
Ogawa (10) Patent No.: US 7,016,523 B1
(45) Date of Patent: Mar. 21, 2006

(54) METHOD FOR OBSERVING OBJECT BY PROJECTION, METHOD FOR DETECTING MICROORGANISMS AND PROJECTION DETECTING SYSTEM

(76) Inventor: Hiroyuki Ogawa, 4-16-308, Nishikicho 2-chome, Aoba-ku, Sendai-shi, Miyagi 980-0012 (JP)

( * ) Notice: Subject to any disclaimer, the term of this patent is extended or adjusted under 35 U.S.C. 154(b) by 0 days.

(21) Appl. No.: 09/556,824

(22) Filed: Apr. 21, 2000

(30) Foreign Application Priority Data

Apr. 21, 1999 (JP) .................................. 11-113059

(51) Int. Cl.
*G06K 9/00* (2006.01)

(52) U.S. Cl. .......................... 382/133; 356/318; 702/21

(58) Field of Classification Search ................ 382/128, 382/133; 356/318, 319; 702/21; 359/391, 359/394
See application file for complete search history.

(56) References Cited

U.S. PATENT DOCUMENTS

| | | | | |
|---|---|---|---|---|
| 3,736,432 A | * | 5/1973 | Sweet | 377/10 |
| 3,819,270 A | * | 6/1974 | Hirschfeld | 356/39 |
| 4,342,515 A | * | 8/1982 | Akiba et al. | 356/237.3 |
| 4,845,552 A | * | 7/1989 | Jaggi et al. | 382/128 |
| 5,739,003 A | * | 4/1998 | Brocklehurst et al. | 435/29 |
| 5,891,394 A | * | 4/1999 | Drocourt et al. | 422/50 |
| 6,002,789 A | * | 12/1999 | Olsztyn et al. | 382/133 |
| 6,122,396 A | * | 9/2000 | King et al. | 382/133 |
| 6,317,511 B1 | * | 11/2001 | Horiuchi | 188/71.6 |
| 6,424,421 B1 | * | 7/2002 | Cremer et al. | 356/620 |
| 6,518,056 B1 | * | 2/2003 | Schembri et al. | 435/287.2 |
| 6,538,819 B1 | * | 3/2003 | Tanaka | 359/619 |

FOREIGN PATENT DOCUMENTS

| | | |
|---|---|---|
| JP | 55-80054 | 6/1980 |
| JP | 03-044765 | 2/1991 |
| JP | 05-269135 | 10/1993 |
| JP | 08-243105 | 9/1996 |
| JP | 10-033542 | 2/1998 |
| JP | 10-090163 | 4/1998 |
| JP | 10-337176 | 12/1998 |
| WO | WO 98/28592 | * 12/1997 |

* cited by examiner

*Primary Examiner*—Samir Ahmed
*Assistant Examiner*—Charles Kim
(74) *Attorney, Agent, or Firm*—Snider & Associates; Ronald R. Snider (57) ABSTRACT

Fast microbial detection is accomplished by identifying quantities of microorganisms accurately and easily.

A cell 5 is placed on a loading portion. A coherent laser beam source 2 emits laser beam to a cell 5. A CCD area image sensor 4 is an array of light sensitive detectors. An image sensor 4 receives light projection image that passes through a cell 5 illuminated by the beam from a laser beam source 2, generating projection image signals on each light sensitive detectors. The projection image data is fed into a computer and analyzed.

14 Claims, 4 Drawing Sheets

METHOD FOR OBSERVING OBJECT BY PROJECTION, METHOD FOR DETECTING MICROORGANISMS AND PROJECTION DETECTING SYSTEM

TECHNICAL FIELD

This invention relates to a method for observing an object, a method for detecting microorganisms in a culture medium, and a projection detecting system for an object.

BACKGROUND ART

For detecting the presence of such microorganism in food as *Escherichia coli, Staphylococcus aureus, Vibrio* or the like, that causes food poisoning, food manufacturing companies work on microbial detection. To express a level of contamination, number of living organisms per 1 g or 1 ml in foodstuff is used as an indicator when microbial detection is performed. Standard Methods Agar is widely used in the determination of microbial counts, being incubated at 35° C.±1° C. for 24 or 48 hours. To determine microbial counts, colonies on an agar plate are counted while viewing the agar plate or a colony counter is used for counting. In count methods, a dilution of the sample is mixed in a sterile dish with melted agar and colonies in a medium are counted after the agar is incubated.

Other approaches to the microbial detection method and system are taught in such Japanese Patent applications as 5-288992 and 10-240950. Such patent applications teach the way to detect microorganisms by processing image data collected with CCD camera, magnifying microorganisms with lenses.

However, traditional approach to the microbial counts have involved longer incubation duration since a colony has to be large enough to be counted visually, and a longer incubation often causes colony overlapping and count difficulty or inaccuracy problem when the contamination level in a sample is high. The method and system taught in Japanese Patent applications as 5-288992 and 10-240950 use lenses to magnify microorganisms so that focussing process is required and only the microorganisms at focal distance can be observed with the technique. The objective of the present invention is to resolve said problems and to provide a method for observing microscopic object by projection, a novel microbial detection method capable of more rapidly determining the presence and quantities of microorganisms accurately and easily, and a projection detecting system capable of facilitating precise microbial detection.

DISCLOSURE OF THE INVENTION

To achieve said objectives, a method for observing an object by projection of the first invention comprises the step of illuminating an object under observation with coherent laser beam receiving the light projection generated by the object under observation with image sensor and producing output of the magnified picture with the projected image data obtained by said image sensor.

With a method for observing object by projection, computer preferably performs magnification of the projected image data obtained by said image sensor and outputs the enlarged picture to a display, a printer or some other output devices.

A method for detecting the presence of microorganisms in a sample of the second invention comprises the step of preparing a light-permeable culture medium mixed with a sample, illuminating said medium with a coherent laser beam, receiving the light projection generated by said medium with an image sensor and detecting the presence of microorganisms by analyzing the projected image data obtained by said image sensor.

An image sensor is preferably CCD (Charge Coupled Device) area image sensor which is an array of light sensitive detector elements, each of which has a side length of few microns. An image sensor preferably faces the laser beam perpendicularly. A light-permeable culture medium preferably contains TTC (Triphenyltetrazolium Chloride) which stains transparent microorganisms and makes them more visible.

The method for detecting the presence of microorganisms in a sample comprises the step of preparing a light-permeable culture medium mixed with a sample, illuminating said medium with a coherent laser beam, receiving the light projection generated by said medium with an image sensor. The image sensor generates light projection detect signal when colonies of microorganisms grow large enough to create shades blocking laser beam. The presence of microorganisms is detected by the shades. With said invention of a method for detecting the presence of microorganisms in a sample, microorganisms such as *Vibrio alginolyticus*, that form transparent colonies, can be detected without staining since the presence of transparent colonies on laser path create ring shaped shades generated by diffraction effect. However, microorganisms such as *Vibrio parahaemolyticus*, that are stainable by some form of dye such as TTC, may be stained to facilitate microbial detection.

A projection detecting system of the third invention is characterized in that it has a loading portion for an object under observation, a coherent laser beam emitting source which illuminates the object placed on said loading portion, an image sensor, which is an array of light sensitive detectors, arranged to receive the light projection generated by said object illuminated by said laser beam and providing the projected image data corresponding to each detector.

When the projection detecting system of the third invention is used, a sample-containing container cell is placed on a loading portion. A sample is mixed with a light-permeable medium and poured into a transparent container cell, for instance. A coherent laser beam emitting source illuminates through the container cell placed on said loading portion and an image sensor receives the light projection generated by the sample-containing medium. When a sample forms colonies, they block the laser beam and create shades and produce the projected image data output on each detector of an image sensor. When an object under observation comprising of a transparent container cell filled with a sample-containing medium is used, for example, and a sample inside forms colonies, the presence of microorganisms in the sample is detected.

A projection detecting system of the fourth invention is characterized in that it has multiple loading portions capable of accommodating many objects under observation in a row, a coherent laser beam emitting source which illuminates through said objects placed on said loading portion, and an image sensor which is an array of light sensitive detectors, arranged to receive the compounded light projection generated by said objects illuminated by said laser beam and providing the projected image data corresponding to each detector.

When the projection detecting system of the fourth invention is used, many sample-containing container cells under observation are placed on multiple loading portions in a row.

A sample is mixed with a light-permeable medium and poured into a transparent container cell, for example. A coherent laser beam emitting source illuminates through many sample-and-medium filled container cells placed on said loading portion and an image sensor receives the compounded light projection generated by said samples. When a sample in each container cell forms colonies, they block the laser beam and create shades and produce the projected image data output on each detector of an image sensor. When objects under observation comprise of transparent container cells filled with a sample-containing medium, for instance, and a sample inside of any container cell forms colonies, blocking the laser beam and creating shades which generate the projected image data corresponding to each detector, the presence of microorganisms in one or more container cells is detected. When the presence of microorganisms is detected in samples, if a laser beam individually illuminates sample by sample, then the specific sample creating shades can be identified. With this set-up, microbial detection becomes more efficient especially when number of samples contaminated by microorganisms is small.

A projection detecting system of the fifth invention is characterized in that it has a loading portion for an object under observation, three coherent laser beam emitting sources which illuminate said object placed on said loading portion from X, Y and Z direction perpendicular to each other, and three image sensors which are an array of light sensitive detectors, arranged to receive the light projection generated by said object illuminated by said laser beams from X, Y and Z direction respectively and providing the projected image data corresponding to each detector as X, Y and Z image data.

When the projection detecting system of the fifth invention is used, a sample-containing container cell is placed on a loading portion. A sample is mixed with a light-permeable medium and poured into a transparent container cell, for instance. Coherent laser beam emitting sources illuminate a sample from X, Y and Z direction and image sensors receive respective X, Y and Z projection image data. The image sensors generate projection image data on each detector when microscopic object of some sort in a sample blocks the laser beams. When an object under observation comprises of a transparent container cell filled with a sample-containing medium, for instance, and a sample inside of container cell forms colonies, blocking the laser beam and creating shades which generate the projected image data corresponding to each detector, the presence of microorganisms in the sample is detected. Using a three-dimensional (3D) projection created by X, Y and Z image data, physical shape of the object is observed and overlapped shades detected by straight one directional beam can be separated and isolated.

A projection detecting system of the sixth invention is characterized in that it has a loading portion which holds an object under observation and is capable of rotating said object with constant angular velocity around center axis that passes through the center of said object, a coherent laser beam emitting source which illuminates said object placed on said loading portion from the direction perpendicular to the axis of rotation, and an image sensor which is an array of light sensitive detectors, arranged to receive the light projection generated by said object illuminated by said laser beam and providing the projected image data corresponding to each detector.

When the projection detecting system of the sixth invention is used, a sample-containing container cell is placed on a loading portion. A sample is mixed with a light-permeable medium and poured into a transparent cylindrical container cell, for example. While rotating the container cell on said loading portion with constant angular velocity around the center of axis that passes through the center of a container cell, a coherent laser beam emitting source illuminates the sample-containing container cell and an image sensor receives the light projection generated by the sample illuminated by the laser beam. The image sensor generates projection image data on each detector when microscopic object of some sort in the sample blocks the laser beam. When an object under observation comprises of a transparent container cell filled with a sample-containing medium for instance, and a sample inside of container cell forms colonies, blocking the laser beam and creating shades which generate the projected image data corresponding to each detector, the presence of microorganisms in a sample is detected. When a projection image data is collected, rotating a sample-containing container cell, physical shape of the object is observed and overlapped shades detected by straight one directional beam can be separated and isolated.

With this invention of a method for detecting the presence of microorganisms in a sample and a projection detecting system, the presence of microorganisms is detected by image sensor so that colonies are detected before they can be seen by naked eye and incubation duration until detection is much shorter. Detecting the presence of microorganisms is also achieved before colonies grow up and overlap each other so that accurate microbial counts can be obtained easily. Furthermore, no troublesome lens focussing is required for microbial detection and all microorganisms in the path of laser beam are detected regardless the depth they locate since microorganisms in a sample are directly projected to image sensor.

With said invention of a method for detecting the presence of microorganisms in a sample and a projection detecting system, graphical image of colonies can be created by the projected image data to be analyzed for its physical shape. Furthermore, microbial counts can be performed, using projected image data for colonies that reached to certain size after certain period of time. Microbial growth time can be obtained by measuring time till colonies grow to certain size to be detected.

Moreover, a selective medium for particular specie and the information on microbial growth rate, colony shape, projected color image data, those which are unique to the microorganism under investigation, can be utilized to identify and determine the species.

BRIEF DESCRIPTION OF THE DRAWINGS

(A) simplified figure of third form of application: a projection detecting system (B) simplified 3D graph of second form of application: X, Y, Z coordination graph

BEST MODE FOR CARRYING OUT THE INVENTION

Figure 1:
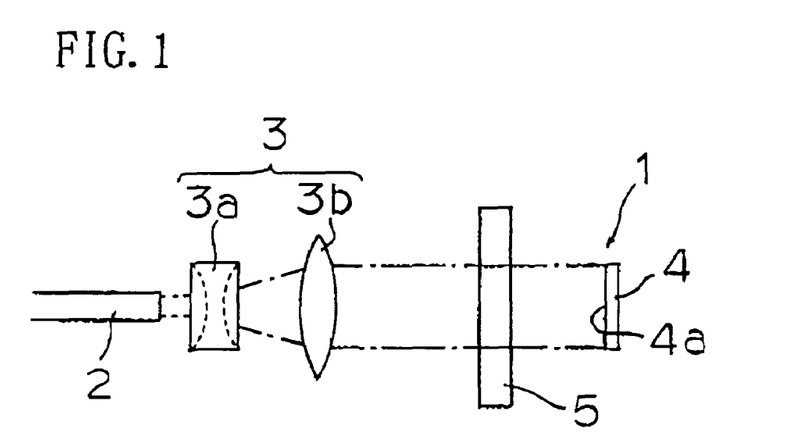
FIG. 1 shows first form of application of a projection detecting system in simplified drawing.

Using figures, some applications of the present invention are described as follows. FIG. 1 shows first form of application of the present invention.

As FIG. 1 shows, a projection detecting system 1 has a loading portion (not shown in the figure), a laser beam emitting source 2, a beam expander 3 and an image sensor 4.

A loading portion accommodates a cell 5 (transparent container for light-permeable medium). A cell 5 utilized is transparent, thin and sterilized 10 ml container cell. A loading portion has a capability of incubating the cell 5 at appropriate temperature for microorganisms to grow. Instead of having incubation ability, cell 5 can be made out from a material that heats up by itself to appropriate temperature for microorganisms to grow, receiving laser beam from a laser beam emitting source 2.

A laser beam emitting source 2 is so arranged to illuminate the cell 5 placed on a loading portion. A white laser is more desirable for a laser beam emitting source 2, but a semiconductor red laser can be used for the purpose, A beam expander 3 that composes of a convex lens 3a and a concave lens 3b, expands the diameter of laser beam emitted by the laser beam source 2, to the larger size of covering the entire image sensor 4.

Figure 2:
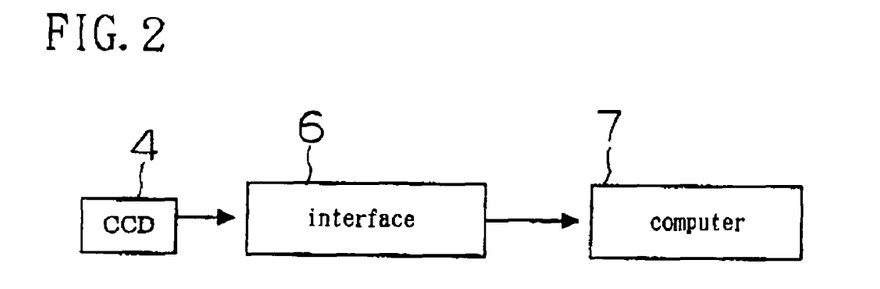
FIG. 2 is hardware configuration block diagram of a projection detecting system shown in FIG. 1.

An image sensor 4 is a CCD (Charge Coupled Device) area image sensor which is an array of light sensitive detectors, each of which has a side length of few microns. For an image sensor 4, interline CCD image sensor TCD5471AD, manufacture by Toshiba, can be used, for example. The particular CCD has 858×614 pixels, detector element size of 5.7 $\mu$m×5.9 $\mu$m and image size of 4.9 mm×3.6 mm. An image sensor 4 is preferably capable of sampling and handling 24 bit color image data (16.700,000 color) when a white laser is used as a beam-emitting source. An image sensor being capable of sampling and handling 8 bit image data (256 separation steps) may be used for the image sensor 4 when a single color laser is used as a beam source. An image sensor 4 is arranged to be located behind a loading portion at the opposite side, facing a laser beam emitting source 2. At a right angle, the sensor surface 4a receives the laser beam which is emitted by a laser beam source 2, expanded by a beam expander 3 and passes through a cell 5. An image sensor 4 is an array of light sensitive detectors that generate projection image signals. As shown in FIG. 2, the projection image data is fed to a computer 7 through an interface 6 and analyzed.

Next, operation is described. When microbial detection is performed with a projection detecting system 1, a sample of 1 ml is mixed with agar medium (light permeable medium) of 9 ml and poured into 10 ml cell 5. A sample could be a piece of foodstuff for example. Agar medium is melted with heat and kept at about 50° C.

To make transparent microorganisms more visible, TTC (Triphenyltetrazolium Chloride) is mixed into the medium. TTC is taken by microorganisms and is reduced to formazan, an insoluble red pigment, by actively growing microbial cells. After closing a lid of a cell 5, a sample and a medium are mixed together and the mixture is solidified to prevent microorganisms to move. The cell 5 is placed at a loading portion. A loading portion is capable of incubating the cell 5 at an appropriate temperature for microorganisms to grow.

A laser beam emitting source 2 illuminates the surface of a cell 5 from a right angle. At a right angle, an image sensor 4 receives laser beam that passes through a medium. When a cell 5 is placed at a loading portion, initial projection image is sampled and kept. It is assumed that the shades on initial projection image are caused by dust of some sort. Then the initial projection image data is kept in a computer 7. If the same shades exist on the projection image from then on, they are ignored.

The image sensor 4 generates light projection detect signal as a graphical data by a detector array, when in an agar medium colonies of microorganisms grow large enough to create shades blocking laser beam. Furthermore, even transparent colonies without staining create shades by diffraction effect and the presence of them can be detected. The projection detect signal is fed to a computer 7 through an interface 6 and analyzed. Then the presence of microorganisms is detected. By sampling image data a few times in an hour to monitor the process of microbial growth, how colonies grow can be observed in a microscopic level. Combined with a computer 7, a projection detecting system 1 can be used as a crude form of microscope.

Sampling a projection data with a CCD image sensor 4, each detector element of which has a size of few microns, is just like observing a microscopic object with a compound eye of few microns each, so to speak. The projection image of microorganisms is obtained by illuminating laser beam through a cell 5 onto the surface 4a of image sensor 4 at a right angle, creating shades of a sample in the cell. When the shades of colonies that grow in binary fission, reach to the size larger than a detector element of CCD image sensor 4, a projection image can be sampled and observed in graphical picture. If there supposed to be a microorganism size of 1 micron and it splits into two in every 20 minutes, becoming double in size, then the colonies become 32 times in size two and half hours later, well exceeding the size of one few-micron-long detector element in a CCD image sensor 4, and the projection of them becomes observable.

Figure 3:
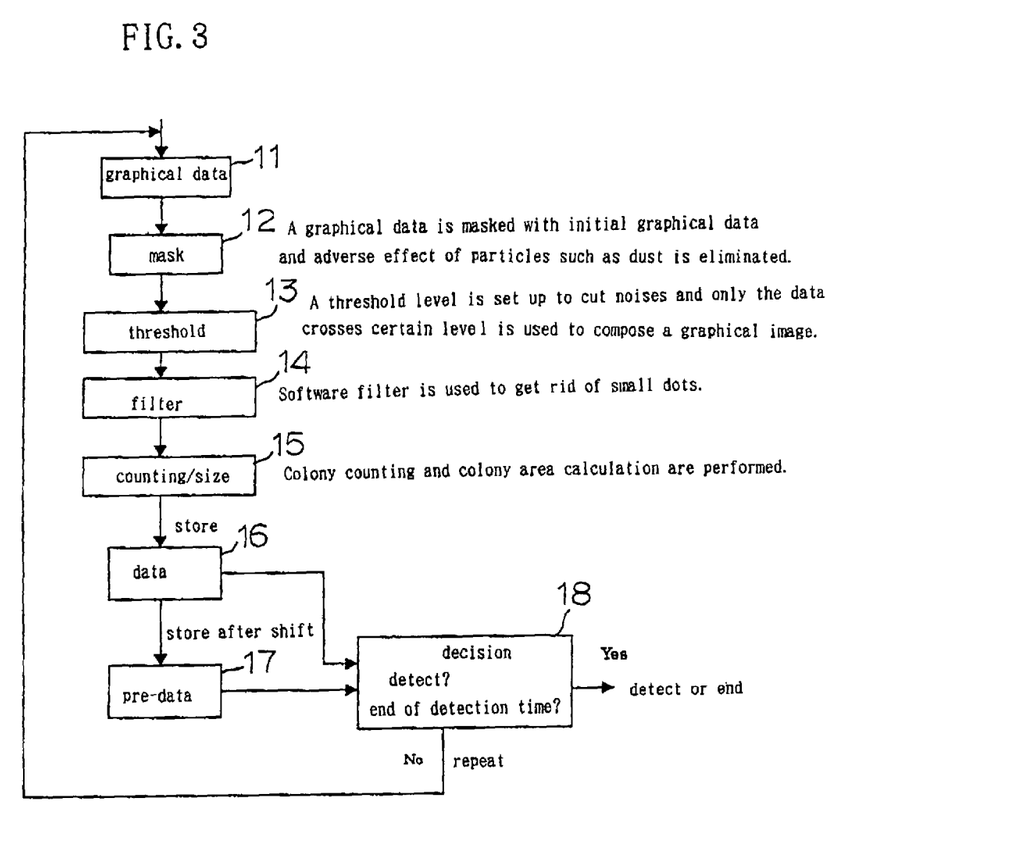
FIG. 3 is software flow chart of microbial detection method when a projection detecting system shown in FIG. 1 is used.

As FIG. 3 shows, software in a computer 7 processes input projection image data as a graphical data, analyzes it, magnifies it and outputs to a display. A graphical data (step 11) is masked with initial graphical data and adverse effect of particles such as dust is eliminated (step 12). If the initial data contains microorganisms larger than an element of image sensor 4 in size, then they grow larger at the sampling time then after so that they can be isolated from dust. At the same time, a threshold level (step 13) is set up to cut noises and only the data crosses certain level is used to compose a graphical image. Software filter (step 14) is used to get rid of small dots and then colony counting and colony area calculation are performed (step 15).

If counts of colonies reache to certain number and do not increase within certain range after sampling image data few times, the counted number is considered as quantities of colonies in a sample. Although the time interval varies from species to species, if no projection image data crossed over threshold level is observed after a few hours of sampling, it is considered that no contamination with microorganisms is detected (step 16,17 and 18).

If a sample of 1 ml is mixed with medium and filled into 10 ml cell 5 and image data is collected and analyzed from one tenth area of image sensor 4, it is essentially same as a sample diluted to one tenth. Therefore, if 10 colonies are detected, analyzing projection image data, then there must be 100 microorganisms exist in a sample of 1 ml.

With a projection detecting system 1, image sensor 4 observes microorganisms in micron level so that incubation time and microbial detection time can be shortened and it is not necessary to incubate long, waiting for colonies to grow visible with naked eye. Since microbial detection is performed while monitoring the process of microbial growth, the presence of microorganisms is detected before colonies overlap each other. Therefore, the system facilitates microbial detection and enables easier and more accurate colony counting possible. In addition to this benefit, image sensor 4 directly receives microorganisms' projection image created by laser beam so that no troublesome lens focussing is required for microbial detection and all microorganisms in the path of laser beam are detected regardless the depth they locate and easier detection is accomplished. With a projection detecting system 1, the process of microbial growth can be monitored while incubating cell 5 at certain temperature. A selective medium for particular specie together with the information database on colony shape, microbial growth rate, projected color image data, those which are unique to the microorganism under investigation, can be utilized to identify and determine the species.

Figure 4:
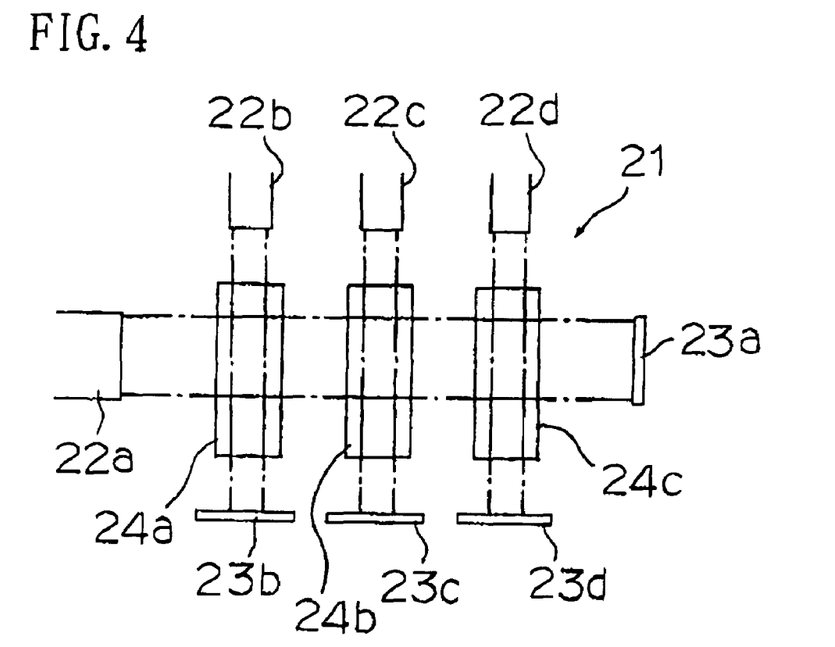
FIG. 4 shows second form of application of a projection detecting system in simplified drawing.

FIG. 4 shows second form of application of the present invention. As FIG. 4 shows, a projection detecting system 21 has multiple loading portions, many laser beam emitting sources 22a~22d, and many image sensor 23a~23d.

Multiple loading portions accommodate cells 24a~24c (transparent container for light-permeable medium). Multiple loading portions have a capability of incubating cells 24a~24c at an appropriate temperature for microorganisms to grow. Cells 24a~24c under observation are placed on multiple loading portions in a row. The same laser beam emitting source previously described in first form of application can be used for each coherent laser beam emitting source 22a~22d. Multiple laser beam emitting sources 22a~22d comprise of laser source 22a for gross check and laser sources 22b~22d for individual check. Laser beam emitting source 22a is arranged to illuminate through cells 24a~24c on multiple loading portions with single beam. Coherent laser beam emitting sources 22b~22d illuminate respective each cell 24a~24c from direction perpendicular to laser beam of emitting source 22a.

The same image sensor previously described in first form of application can be used for each image sensor 23a~23d. Image sensors 23a~23d are an array of light sensitive detectors, arranged to receive the light projection to provide projection image data output. Bach image sensor 23a~23d is arranged to be located behind multiple loading portions at the opposite side, facing laser beam emitting sources 22a~22d. At a right angle to the surface, image sensor 23a receives the laser beam which is emitted by a laser beam source 22a and passes through multiple cells 24a~24c. At a right angle to the surface, image sensors 23b~23d are arranged to receive the laser beam, which is emitted by a laser beam sources 22b~22d and passes through cells 24a~24c from the direction perpendicular to a laser beam emitted by beam source 22a. As shown in FIG. 2, the projection image data is fed to a computer 7 through an interface 6 and analyzed.

Next, operation is described. When a projection detecting system 21 is used, many sample-containing container cells 24a~24c under observation are placed on multiple loading portions in a row. A sample is mixed with a light-permeable medium, poured into a transparent container cells 22b~22d, and solidified. A coherent laser beam emitting source 22a illuminates through many sample-and-medium filled container cells 24a~24c. At a right angle to the surface, an image sensor 23a receives the compounded light projection generated by the samples and generates light projection detect signal when colonies in either sample grow large enough to create shades blocking laser beam. The presence of microorganisms in either one of multiple samples is detected by this way. A laser beam emitting source 22a is used for monitoring microbial growth.

When the presence of microorganisms is detected in samples with a laser beam of emitting source 22a, laser beam emitting sources 22b~22d individually illuminate each cell 24a~24c, cell by cell, from the direction perpendicular to the laser beam emitted by source 22a, and image sensors 23b~23d receive those beams at a right angle. Each image sensor 23b~28d generates light projection detect signal when colonies of microorganisms grow large enough to create shades blocking laser beam. As shown in FIG. 2, software on a computer 7 processes projection image data, analyzes it, magnifies it and outputs to a display device. By doing this way, the specific sample contaminated by microorganisms can be identified. With a projection detecting system 21, microbial detection becomes more efficient, handling many samples at a time, especially when number of samples contaminated by microorganisms is small.

Figure 5:
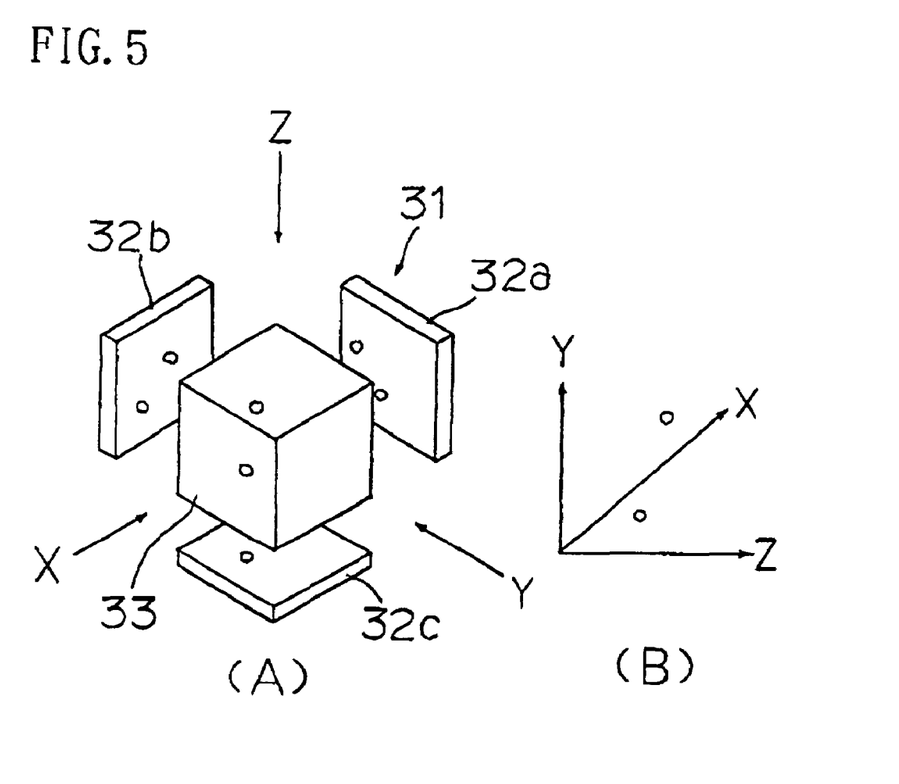
FIG. 5 shows third form of application of a projection detecting system in simplified drawing.

FIG. 5 shows third form of application of the present invention. As FIG. 5(A), (B) show, a projection detecting system 31 has a loading portion, coherent laser beam emitting sources (not shown in the figure) and image sensors 32a~32c. A loading portion accommodates a cube cell 33 (transparent container for light-permeable medium). A loading portion has a capability of incubating the cube cell 33 at appropriate temperature for microorganisms to grow. The same laser beam emitting source previously described in first form of application can be used for each coherent laser beam emitting source. Coherent laser beam emitting sources illuminate a cube cell placed on a loading portion from X, Y and Z direction perpendicular to each other.

The same image sensor previously described in first form of application can be used for image sensors 32a~32c. Image sensors 32a~32c are an array of light sensitive detectors, arranged to receive the light projection to provide projection image data output. Each image sensor 32a~32c is arranged to be located behind a loading portion at the opposite side, facing laser beam emitting source. At a right angle to the surface, image sensors 32a~32c are arranged to receive the light projection generated by a cube cell 33 illuminated by laser beams from X, Y and Z direction respectively. The projection image data is fed to a computer 7 through an interface 6 and analyzed (refer to FIG. 2).

Next, operation is described. When a projection detecting system 31 is used, a cube cell 33 under observation is placed on a loading portion. A sample is mixed with agar medium (a light-permeable medium), poured into a transparent cube cell 33 and solidified. Coherent laser beam emitting sources illuminate a cube cell 33 from X, Y and Z direction and at a right angle to the surface, image sensors 32a~32c receive respective X, Y and Z projection image data which are generated by a sample in a cube cell. The image sensors 32a~32c generate projection image data on each detector when colonies in a sample medium grow and block the laser beams. By this way, the presence of microorganisms in the sample is detected. The X, Y and Z projection signals generated by shades are fed to a computer 7 through an interface 6 and a three-dimensional image is created from X, Y and Z projection image data. The 3D image is magnified and displayed. Using 3D image created by X, Y and Z image data, physical shape of the colonies is observed and overlapped colonies detected by straight one directional beam can be separated and isolated. In addition, if a pair of a white laser and a color CCD is used, microorganisms can be characterized by color components.

Figure 6:
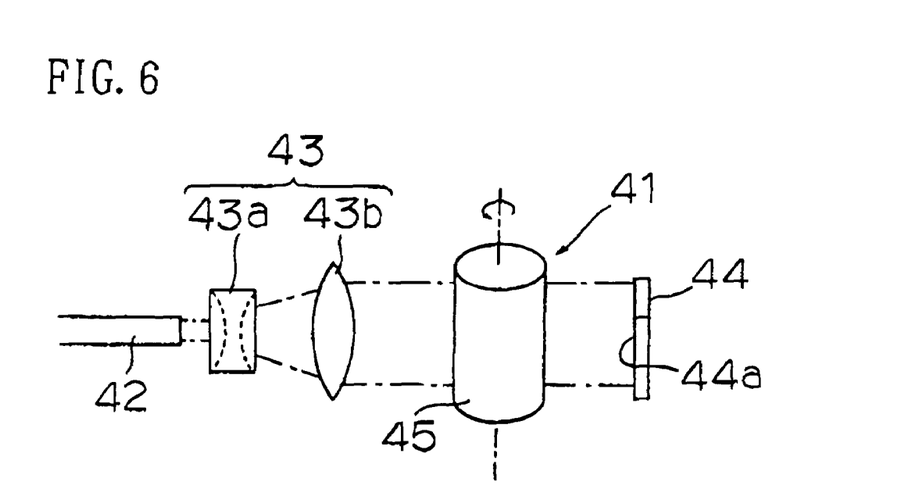
FIG. 6 shows fourth form of application of a projection detecting system in simplified drawing.

FIG. 6 shows fourth form of application of the present invention. As FIG. 6 shows, a projection detecting system 41 has a loading portion, coherent laser beam emitting sources 42, beam expander 43 and image sensors 44.

A loading portion accommodates a cylindrical container cell 45 (transparent container for light-permeable medium). A loading portion has a capability of incubating the cylindrical container cell 45 at appropriate temperature for microorganisms to grow. A loading portion holds a cylindrical cell 45 and is capable of rotating the cell with constant angular velocity around center axis that passes through the center of cylindrical cell. The same laser beam emitting source previously described in first form of application can be used for a coherent laser beam emitting source 42. A coherent laser beam emitting source 42 is arranged to illuminate a cell 45 placed on a loading portion from the direction perpendicular to the axis of rotation. A beam expander 43 composes of a convex lens 43a and a concave lens 43b and expands the diameter of laser beam, that is emitted by the laser beam source 44, to the larger size of covering the entire image sensor 44.

The same image sensor previously described in first form of application can be used for an image sensor 44. An image sensor 44 is an array of light sensitive detectors, arranged to receive the light projection to provide projection image data output. An image sensor 44 is arranged to be located behind a loading portion at the opposite side, facing a laser beam emitting source 42 and receives the beam at a right angle. The projection image data is fed to a computer 7 through an interface 6 and analyzed (refer to FIG. 2).

Next, operation is described. When a projection detecting system 41 is used, a cylindrical cell 45 under observation is placed on a loading portion. A sample is mixed with agar medium (a light-permeable medium), poured into a transparent cylindrical cell and solidified. While rotating the cylindrical cell 45 on a loading portion with constant angular velocity around the center of axis that passes through the center of cylindrical cell, a coherent laser beam emitting source 42 illuminates the sample-containing cylindrical cell and an image sensor 44 receives the light projection generated by the sample illuminated by the laser beam at a right angle. An Image sensor 44 generates the projected image data, receiving the light projection, when a sample inside of cell forms colonies, blocking the laser beam and creating shades.

By sampling image data a few times in an hour to monitor the process of microbial growth, the presence of microorganisms is detected in a microscopic level. Software creates three-dimensional image on a computer 7, to which the projection image data is fed in through interface 6, while rotating a cell 45 one turn or 360 degrees (refer to FIG. 2). 3D image is magnified and displayed. With 3D image, physical shape of colonies is observed and overlapped shades detected by straight one directional beam can be separated and isolated. Well-trained lab technologists may be able to identify the species of microorganisms by looking at the shape and color of 3D colony image. Furthermore, if data on shape and color of colonies of microorganisms are accumulated to build up database, automatic identification on microorganisms by software is possible to achieve.

When the present invention is applied, following benefits can be realized, (a) a method for facilitating observation of microscopic object by projection, (b) a novel microbial detection method capable of more rapidly determining the presence of microorganisms and identifying quantities of them accurately and easily while shortening incubation duration, (c) and a projection detecting system capable of facilitating a precise microbial detection.

Note that the aforementioned disclosure claims the priority of and relates to the subject matter contained in Japanese Patent Application No. 11-113059 filed on Apr. 21, 1999, which is incorporated by reference in this application in its entirety.

What is claimed is:

1. A method for detecting the presence of colonies of microorganisms in a sample, comprising the step of:
   (a) preparing a light-permeable microorganism colony culture medium mixed with a sample;
   (b) pouring said microorganism colony culture mixture into a transparent container cell;
   (c) solidifying said microorganism colony culture in said container cell;
   (d) illuminating said container cell and medium with a coherent laser beam;
   (e) receiving the light projection generated by said colony culture medium with an image sensor;
   (f) detecting the presence of colonies of microorganisms by analyzing the projected image data obtained by said image sensor after colonies grow large enough to create shades on the image sensor and the colonies block the laser beam to produce projected image data of the colonies on the image sensor based on the unblocked illumination of the laser beam.

2. The method of detecting colonies of microorganisms in accordance with claim 1, wherein the container cell is cylindrical.

3. The method of detecting colonies of microorganisms in accordance with claim 2, comprising the step of rotating the container cell with constant angular velocity around a center axis that passes through the center of said object during said detecting step.

4. The method of detecting microorganisms in accordance with claim 1, wherein the container cell is rotated about an axis that passes through a center of the container cell when illuminated with the laser beam.

5. The method of detecting microorganisms in accordance with claim 1, wherein the presence of microorganisms is detected before colonies overlap each other.

6. The method of detecting colonies of microorganisms in accordance with claim 1, further comprising the step of detecting a number of colonies to express a level of contamination in a food stuff.

7. The method of detecting colonies of microorganisms in accordance with claim 1, further comprising the step of allowing said colonies to grow large enough to produce image output data on an image detector having an area greater than one micron in size.

8. The method of detecting colonies of microorganisms in accordance with claim 1, further comprising the step of detecting all microorganism colonies in the path of the laser beam regardless of depth of location by projecting a colony image directly onto the image sensor.

9. The method of detecting colonies of microorganisms in accordance with claim 1, further comprising the step of staining said colonies with triphenyltetrazolium chloride.

10. A projection detecting system comprising:
   (a) a loading portion of a transparent sample containing nonflowing cell container which contains a light permeable microorganism colony under observation;
   (b) a coherent laser beam emitting source which illuminates the object placed on said loading portion;
   (c) an array of light sensitive detectors; arranged to receive light projection generated by said object illuminated by said laser beam and providing projected image data corresponding to each detector; and (d) an illumination system which projects light from said laser beam emitting source onto an image sensor which consists of a beam expander placed between said laser beam emitting source and said loading portion;

(e) wherein the presence of colonies of microorganisms are detected by analyzing the projected image data obtained by said image sensor after colonies grow large enough to create shades on the image sensor and the colonies block the laser beam to produce projected image data of the colonies on the image sensor based on the unblocked illumination of the laser beam.

11. The projection detecting system as described in claim 10 comprising:

(a) multiple loading portions capable of accommodating many of said transparent nonflowing cell containers under observation in a row;

(b) a coherent laser beam emitting source which illuminates through said transparent nonflowing cell containers placed on said loading portion; and (c) an image sensor which is an array of light sensitive detectors, arranged to receive the compounded light projection generated by said transparent nonflowing cell containers illuminated by said laser beam and providing the projected image data corresponding to each detector.

12. The projection detecting system as described in claim 10 comprising:

(a) three coherent laser beam emitting sources which illuminate said transparent nonflowing cell container placed on said loading portion from X; Y and Z directions which are perpendicular to each other; and (b) three image sensors which are an array of light sensitive detectors, arranged to receive the light projection generated by said object illuminated by said laser beams from X, Y and Z directions respectively and providing the projected image data corresponding to each detector as X, Y and Z image data.

13. The projection detecting system as described in claim 10 comprising:

(a) a loading portion which holds a transparent nonflowing cell container which contains a microorganism colony under observation and which rotates said object with constant angular velocity around center axis that passes through the center of said object during measurement;

(b) a coherent laser beam emitting source which illuminates from the direction perpendicular to the axis of rotation.

14. The projection detecting system as described in claim 10, wherein said beam expander consists of a concave lens and a convex lens.

* * * * *